United States Patent [19]

Prakash

[11] Patent Number: 5,395,753
[45] Date of Patent: Mar. 7, 1995

[54] METHOD FOR DIAGNOSING RHEUMATOID ARTHRITIS

[75] Inventor: Ramesh K. Prakash, Salt Lake City, Utah

[73] Assignee: Theratech, Inc., Salt Lake City, Utah

[21] Appl. No.: 19,780

[22] Filed: Feb. 19, 1993

[51] Int. Cl.6 .......................... C12Q 1/00; C12Q 1/68; G01N 33/53; G01N 33/564

[52] U.S. Cl. .......................................... 435/7.1; 435/5; 435/6; 435/7.9; 435/7.92; 435/21; 436/506; 436/513; 436/543

[58] Field of Search ................. 435/7.92, 69.3, 5, 6, 435/7.1, 7.9, 7.92, 21; 436/506, 513, 543

[56] References Cited

PUBLICATIONS

Kemp, M. et al.; Biol. Abstracts 81:63056 (1986).
Habets, W. J. A. et al.; Clin. Exp. Immunol. 76:172 (1989)
Kunakorn, M. et al.; J. Clin. Microbiol. 28:1249–1253 (1990).
Jirik, F. R. et al.; Proc. Natl. Acad. Sci. USA 83:2195–2199 (1986).
Artandi et al., J. Immunol. 146(2):603–610 (1991).
Halpert et al., Am. J. Clin. Pathol. 74:776–784 (1980).
Dillon et al. (EDS.), *Recombinant DNA Methodology*, John Wiley & Sons, New York, N.Y., 1985, pp. 83–88.

*Primary Examiner*—Robert A. Wax
*Assistant Examiner*—Eric Grimes
*Attorney, Agent, or Firm*—Thorpe, North & Western

[57] ABSTRACT

A method is described for diagnosing rheumatoid arthritis by providing a recombinant IgM-specific rheumatoid arthritis-associated antigen and detecting antibodies against the antigen in patient sera. Preliminary steps of making a cDNA library from polyadenylated RNA purified from human cells, selecting recombinants that express the antigen, recloning cDNA containing the antigen gene in a high level expression vector, expressing the antigen in transformed cells, and purifying the antigen are also described.

23 Claims, No Drawings

METHOD FOR DIAGNOSING RHEUMATOID ARTHRITIS

BACKGROUND OF THE INVENTION

This invention relates to a method for diagnosing rheumatoid arthritis. More particularly, this invention relates to a method for objectively diagnosing rheumatoid arthritis by quantitative determination of the presence or absence of rheumatoid arthritis-associated antibodies in patient sera that react with a recombinant antigen.

Rheumatoid arthritis is a chronic systemic rheumatic disease that affects a significant percentage of the population. Traditionally, it has been diagnosed subjectively through clinical observation and dominant complaints by a patient. P. Lipsky, *Rheumatoid Arthritis*, in Harrison's Principles of Internal Medicine 1423 (1987). Thus, clinical diagnosis of rheumatoid arthritis is subject to the skill of the diagnostician and the severity of disease symptoms in the patient.

For an objective diagnosis of rheumatoid arthritis, the presence of rheumatoid factor (Rf) in the serum of rheumatoid arthritis patients is routinely determined. Rf has been detected in approximately 70% of patients exhibiting clinical symptoms of rheumatoid arthritis. These patients are thus termed "seropositive." The remaining 30% are classified as having "seronegative" rheumatoid arthritis. Numerous conditions besides rheumatoid arthritis are associated with the presence of rheumatoid factor. Therefore, the presence of Rf does not establish a conclusive diagnosis of rheumatoid arthritis. An objective method of diagnosing rheumatoid arthritis that is more closely correlated with clinical diagnoses than is the presence of Rf in sera is needed. Ideally, such an objective diagnostic test would be quick and easy to perform and would not involve radioisotopes or be invasive to the patient.

Sera from patients with various autoimmune rheumatic diseases contain circulating autoantibodies that are directed against cellular, mainly nuclear, components. E. Tan, 33 Advances in Immunology 167–240 (1982). These antibodies, designated as antinuclear antibodies (ANA), are specific for their respective autoimmune diseases and have been useful as diagnostic aids in clinical medicine. Some of the antigens against which these antibodies are directed have been produced by methods of biotechnology and used in diagnosis of respective autoimmune diseases. R. Michael & J. Keene, *Molecular Biology of Nuclear Autoantigen*, in 18 Rheumatoid Disease Clinics of North America 283–310 (D. Pisetsky, ed., 1992). Success in developing diagnostic tests against these autoimmune diseases suggests that a similar approach might be fruitful for rheumatoid arthritis.

Sera from rheumatoid arthritis patients have also been found to contain antibodies to cellular components. A precipitin line formed in agar gel diffusion tests when sera from rheumatoid arthritis patients and extracts of certain Epstein-Barr virus-transformed human B lymphocyte cell lines, such as the WIL-2 and Raji cell lines, were placed in adjacent wells. M. Alspaugh & E. Tan, 19 Arthritis and Rheumatism 711–19 (1976). The antibody responsible for the precipitate was found to be of the IgG type and the antigen against which it reacted was a nuclear antigen. Thus, the antigen was termed "rheumatoid arthritis nuclear antigen" or "RANA."

Several problems would need to be overcome before a diagnostic test based on the presence of RANA could be developed. The identity of the antigen is not known. Even if it were known, it occurs in small quantities in cells and would be difficult to purify to homogeneity. Such purity is needed because false positives might result if contaminants were copurified with the RANA, given the extreme sensitivity of serological tests that can be devised to detect small quantities of antigen.

OBJECTS AND SUMMARY OF THE INVENTION

It is an object of the present invention to provide a method for diagnosing rheumatoid arthritis.

It is another object of the invention to provide a method for diagnosing rheumatoid arthritis by serological analysis of patient sera.

It is also an object of the invention to provide a method for diagnosing rheumatoid arthritis by ELISA analysis of patient sera.

It is a further object of the invention to provide a nucleic acid vector capable of directing expression of a recombinant antigen detectable by rheumatoid arthritis-associated antibodies.

It is still another object of the invention to provide a recombinant antigen detectable by rheumatoid arthritis-associated antibodies.

It is yet another object of the invention to provide a method for isolating a recombinant antigen detectable by rheumatoid arthritis-associated antibodies.

These and other objects may be accomplished by providing a recombinant antigen and detecting rheumatoid arthritis-associated antibodies in patient sera directed against the antigen. Preliminary steps to providing the recombinant antigen include making a cDNA clone library from polyadenylated RNA purified from human Raji cells, selecting recombinants from the library that express the recombinant antigen with antibodies in serum from a rheumatoid arthritis patient, recloning the cDNA from a selected recombinant in an expression vector, expressing the cloned recombinant antigen in appropriate cells, and purifying the recombinant antigen. The purified recombinant antigen can then be used as a reagent to test patient sera by sensitive methods such as ELISA.

DETAILED DESCRIPTION

Purification of Polyadenylated RNA

Polyadenylated mRNA was isolated using the "FAST TRACK" mRNA isolation kit, purchased commercially from Invitrogen (San Diego, Calif.). In this procedure, about $1 \times 10^8$ human Raji cells, available from the American Type Culture Collection (accession no. CCL 86), were grown in RPMI-1640 medium (Hyclone, Logan, Utah) and then washed in PBS. The Raji cells were suspended and lysed in 15 ml of a lysis buffer containing 1 volume of stock buffer (200 mM NaCl, 20 mM Tris.HCl, pH 7.5, 1.5 mM $MgCl_2$, 2% SDS) and 0.02 volumes of RNase Protein Degrader. The lysate was poured into a sterile 50 ml Dounce homogenizer at room temperature and homogenized with 10–12 up and down strokes or until the viscosity of the lysate was about the same as the lysis buffer. An alternative method of homogenizing the cells is to pass the lysate through a sterile plastic syringe fitted with an 18 gauge needle.

The homogenized lysate was then incubated in the lysis buffer at 45° C. for 1–2 hours in a shaking water bath. This step of the procedure is important for proteolytic digestion of proteins including ribonucleases. Then the NaCl concentration of gthe lysate was adjusted to 0.5M by the addition of an appropriate amount of 5M NaCl stock solution. The original NaCl concentration of the lysis buffer was 0.2M, thus addition of 0.95 ml of 5M NaCl raised the NaCl concentration to the desired level. The lysate was then mixed thoroughly.

Oligo(dT) cellulose was hydrated and pre-equilibrated before use. Fifty milligrams of oligo(dT) cellulose was placed in a sterile 50 ml conical centrifuge tube and incubated with 2 ml of sterile water for 1 hour at room temperature. The hydrated oligo(dT) cellulose was then centrifuged for 1–3 minutes at 6000 rpm in a table top centrifuge to form a pellet. The supernatant liquid was removed, 5 ml of Binding Buffer (0.01M Tris.HCl, pH 7.6, 0.5M NaCl) was added to the pellet, and the oligo(dT) cellulose was resuspended in the buffer. The oligo(dT) cellulose was centrifuged again as before, the supernatant liquid was removed, and the pellet was resuspended in 5 ml of Binding Buffer. Then, the steps of centrifuging, decanting, and resuspending were repeated and the oligo(dT) cellulose was stored at room temperature until the lysate was added.

Then the lysate was added to the pre-equilibrated oligo(dT) cellulose and rocked at room temperature for 20–60 minutes. At this stage of the procedure the polyadenylated RNA hybridized with the oligo(dT) and, thus, was bound to the oligo(dT) cellulose. Then, the oligo(dT) cellulose containing bound polyadenylated RNA was centrifuged at 6000 rpm for 1–3 minutes in a table top centrifuge. The supernatant liquid was removed from the pellet and the pellet was resuspended in 20 ml of binding buffer. The oligo(dT) cellulose was then centrifuged again, the supernatant liquid removed, and the pellet resuspended in 10 ml of Binding Buffer. This process of washing in 10 ml of Binding Buffer was repeated until the supernatant liquid was clear.

The washed oligo(dT) cellulose with bound polyadenylated RNA was then packed in a disposable column supplied with the kit. The oligo(dT) cellulose was washed with Binding Buffer until the $OD_{260}$ of the buffer coming through the column was less than 0.05. Non-polyadenylated RNAs, chromatin DNA, dissolved membranes, proteins, and cell debris were washed off the column in this washing process. The column was then allowed to run dry or until no liquid remained on top of the oligo(dT) cellulose.

The polyadenylated RNA bound to the column was then eluted in low salt buffer (0.01M Tris-HCl, pH 7.6, 0.01M NaCl) in a volume of 1–2 ml. Fractions of 0.3–0.5 ml each were collected in sterile RNase-free microfuge tubes. The polyadenylated RNA generally eluted in the first four fractions. The RNA-containing fractions were pooled and the RNA was precipitated by addition of 0.1 volume of 2M sodium acetate, supplied with the kit, and 2 volumes of ethanol.

This polyadenylated RNA was then used as template material to prepare double-stranded cDNA using a commercial kit (λ Librarian) purchased from Invitrogen. The method used in this kit is the method described by Okayama and Berg, 2Molecular and Cellular Biology 161 (1982), and Gubler and Hoffman, 25 Gene 263 (1983).

cDNA First Strand Synthesis

The first step in making double-stranded cDNA is reverse transcriptase-catalyzed synthesis of single cDNA strands that are complementary to the RNA strands. Polyadenylated RNA dissolved in pure sterile water (2–10 μg in 40–120 μl) was placed in a sterile RNase-free microfuge tube on ice. To the RNA solution was added 12.5 μl of 0.1M methylmercury (II) hydroxide. The contents of the tube were mixed gently by tapping the tube, spinning momentarily in a microfuge, and letting the solution stand for 7 minutes at room temperature. Then, 25 μl of sterile water and 11 μl of 0.7M 2-mercaptoethanol were added. The contents of the tube were mixed gently by tapping the tube, spinning momentarily in a microfuge, and letting the tube stand for 5 minutes at room temperature. These steps yielded RNA that was fully denatured without any internal secondary structure that might have inhibited cDNA synthesis.

The tube was then place on ice and the following ingredients were added in order: 1 μl of oligo(dT) primers, 2 μl of placental ribonuclease inhibitor, 50 μl of 5× reverse transcriptase buffer, 5 μl of a solution containing 25 mM of each of the four deoxynucleoside triphosphates, 10 μl of an $\alpha$-$^{32}$P-labelled deoxynucleoside triphosphate (about 10 μCi), and 6 μl of reverse transcriptase. Sterile water was added to raise the final volume to 250 μl. The contents of the tube were gently mixed by tapping the tube and spinning momentarily in a microfuge. The tube was then place in a 42° C. water bath for 90 minutes. The synthesis reaction was stopped by placing the tube on ice and adding 10 μl of 0.5M EDTA and 250 μl of 1:1 phenol/chloroform. The contents of the tube were mixed vigorously with a vortexer. Then the organic and aqueous phases were separated by centrifugation in a microfuge for 1–2 minutes. The bottom organic layer was removed with a pipettor and was discarded. The aqueous phase containing the RNA and cDNA was kept in the original tube. Proteins, such as reverse transcriptase, were denatured by the phenol/chloroform extraction and removed with the organic layer.

The RNA and cDNA were alcohol precipitated from the aqueous phase by adding 250 μl of 4M ammonium acetate and then 1.0 ml of cold (−20° C.) ethanol. The contents of the tube were mixed vigorously with a vortexer and then the tube was placed on powdered dry ice until the contents were completely solid (about 10 minutes). Then, the solution was thawed and the tube was centrifuged for 15 minutes at 4° C. to pellet the RNA and cDNA. The supernatant liquid was carefully removed, so that the pellet was not disturbed, and discarded. The pellet was resuspended in 100 μl of sterile water with brief vortexing and spinning in a microfuge. Alcohol precipitation was repeated by adding 100 μl of 4M ammonium acetate and 400 μl of cold ethanol, freezing on dry ice, thawing, centrifuging, and removing the supernatant liquid as before. The pellet was then washed by adding 500 μl of cold 80% ethanol, rocking the tube back and forth twice, centrifuging for 5 minutes, and removing the ethanol supernatant. Care was taken not to dry the pellet at this stage.

cDNA Second Strand Synthesis

The cDNA produced by first strand synthesis were hydrogen bonded to the template RNA strands in the form of RNA/DNA hybrids. In performing second strand synthesis, the RNA strands were nicked and partially removed by digestion with *E. coli* RNase H, which specifically cleaves RNA in RNA/DNA hybrids. Fragments of RNA remained duplexed with the first cDNA strands. These RNA fragments were then used as primers for *E. coli* DNA polymerase I catalyzed synthesis of the second cDNA strands. Nicks in the phosphodiester backbone of the cDNA were repaired enzymatically with *E. coli* DNA ligase. These manipulations were performed as follows: The cDNA/RNA pellet was resuspended in 33.5 μl of sterile water. Vortexing and brief centrifugation in a microfuge reduced the time needed for resuspension. The tube was then placed on ice and the following ingredients were added: 5 μl of 10× second strand buffer, 2.5 μl of 1.0 mg/ml BSA, 1 μl of 10 mM β-NAD+, 2 μl of a solution containing 5 mM of each of the four deoxynucleoside triphosphates, 4 μl of RNase H/*E. coli* DNA ligase, and 2 μl of DNA polymerase I. The contents were mixed by tapping the tube and spinning momentarily in a microfuge. The reaction mixture was then incubated for 60 minutes at 15° C. and for an additional 60 minutes at room temperature. The reaction was stopped by heating at 70° C. for 10 minutes. Then the tube was spun briefly in a microfuge, incubated for 2 minutes at room temperature, and chilled on ice.

The end product of this series of reactions was double-stranded cDNA with many molecules having unbasepaired 3' ends on the first strand of cDNA. Further, many molecules of double-stranded cDNA had ribonucleotide residues at the 5' end of the second cDNA strand. For efficient molecular cloning of these cDNA molecules, these ends had to be polished or caused to be blunt ended. This result was achieved by treatment with T4 polymerase. Thus, 3.5 μl of T4 DNA polymerase was added to the reaction mixture and mixed by tapping the tube and spinning briefly in a microfuge. The reaction mixture was incubated for 10 minutes at 37° C., after which the reaction was stopped by adding 2 μl of 0.5M EDTA. Then the cDNA was again phenol/chloroform extracted and alcohol precipitated: 50 μl of 1:1 phenol/chloroform was added to the reaction mixture, the contents of the tube were vortexed, and then the tube was centrifuged for 1 minute to separate the phases. The phenol/chloroform layer was removed from beneath the aqueous layer with a pipettor and then discarded. The aqueous layer was saved and 56 μl of 4M ammonium acetate and 224 μl of cold ethanol were added and mixed thoroughly. The contents of the tube were then frozen on dry ice, thawed, centrifuged at 4° C. for 10-15 minutes, and the ethanol supernatant was removed. The pellet was washed in 500 μl of cold 80% ethanol as before. The ethanol was then removed from the tube, but the pellet was not permitted to dry.

Addition of Linkers to Double-Stranded cDNA

Blunt ended double-stranded cDNA can be cloned efficiently by modifying the ends of the cDNA to have cohesive or staggered ends compatible with cloning at a convenient staggered-end restriction site of a cloning vector. The cDNA was treated to be compatible with cloning at EcoRI sites by adding EcoRI linkers to the blunt ends of the cDNA. The linkers had the following sequence:

AATTCGCGGCCGC(SEQ ID:NO:1)
GCGCCGGCG

The 5' end of the shorter oligomer comprising the linker was phosphorylated whereas the 5' end of the longer oligomer (SEQ ID:NO:1) was not. Consequently, ligation of the linker to blunt-ended cDNA resulted in only one copy of the linker being added per cDNA end since the linker could not be self-ligated at the cohesive ends because of the lack of a phosphate to complete the phosphodiester bond between adjacent nucleotides.

The linkers were added to the double-stranded cDNA by first resuspending the cDNA pellet from the second strand synthesis reaction in 22 μl of sterile water with brief vortexing. The following ingredients were then added in order: 3 μl of 10× ligation buffer, 3 μl of EcoRI linkers (1 μg/μl), and 2 μl of T4 DNA ligase. These components were mixed by brief vortexing and momentary spinning in a microfuge. The tube and contents were then incubated overnight at 15° C. The reaction was stopped by addition of 2 μl of 0.5M EDTA and 50 μl of phenol/chloroform. Phenol/chloroform extraction was performed as previously described. Alcohol precipitation was performed by addition of 3.5 μl of 2M sodium acetate and 70 μl of cold ethanol to the aqueous phase. The solution was mixed and then frozen on dry ice. The precipitated cDNA was recovered by thawing, centrifuging for 15 minutes at 4° C., and carefully removing the ethanol. Then the cDNA pellet was washed in 80% ethanol as previously described. The ethanol supernatant was carefully removed, but the pellet was not permitted to dry.

Once the linkers had been added, the cDNA was treated with T4 polynucleotide kinase to phosphorylate the protruding 5' end of the EcoRI linker. This step was accomplished by resuspending the cDNA pellet in 12 μl of sterile water with brief vortexing. Then 1.5 μl of 10× kinase buffer and 2.0 μl of T4 polynucleotide kinase (5 U/μl) were added to the tube with brief vortexing and centrifugation in a microfuge to mix the components. The reaction was incubated for 30 minutes at 37° C., after which the reaction was stopped by chilling on ice.

Size Selection of cDNA

The double-stranded cDNA resulting from these procedures included a distribution of various lengths of cDNA as well as excess unreacted linkers. The unreacted linkers were removed and cDNA in the range of 1-5 kbp was selected by fractionating the cDNA by electrophoresis in an agarose gel. A 1% agarose gel in Tris-acetate buffer was prepared with agarose powder and Trisacetate buffer supplied in the Invitrogen kit. To the cDNA from the T4 kinase treatment was added 5 μl of Tris-RNase A. The contents of the tube were mixed by brief vortexing and centrifugation in a microfuge, after which they were incubated for 5 minutes at 37° C. This RNase digestion step removed any RNA still remaining in the cDNA and helped improve resolution on the agarose gel. Then, 5 μl of loading dye was added and mixed to the cDNA, followed by incubation for 5 minutes at 37° C. The cDNA was loaded in a middle lane of the gel and 10 μl of DNA molecular weight markers supplied with the kit were loaded in a lane three lanes away from the cDNA lane. Electrophoretic fractionation was at 40-50 volts until the blue dye was half way down the gel, about 2-3 hours.

After fractionation was complete, the gel was removed from the gel apparatus and placed on a sheet of cellophane. The gel was cut lengthwise between the cDNA and marker lanes. The part of the gel containing the cDNA was wrapped in cellophane while the gel portion containing the markers was stained in ethidium bromide using 30 μl of the ethidium bromide stock solution provided in the kit diluted in 250 ml of distilled water. The gel halves were then placed back together and aligned on a fresh piece of cellophane on a UV transilluminator. The marker bands were visualized with UV light and slices of the cDNA lane were cut corresponding to the desired size of 1–5 kbp. The gel slices were cut into 4–6 smaller pieces and the cDNA was immediately electroeluted.

Electroelution was accomplished using a disposable electroelution cartridge supplied with the kit. The device held the excised agarose pieces in its barrel while electrophoretic potential eluted the cDNA through a microporous polyethylene frit and against a window of dialysis membrane. The frit prevented minute fragments of agarose and polymer complexes from contaminating the cDNA. The cDNA was electroeluted in 0.25× Tris-acetate buffer at 150 volts for 2–3 hours. The cDNA held against the dialysis membrane window was resuspended by pipetting 300–350 $\mu$l of buffer against the window several times. The eluted cDNA was then place in a siliconized tube supplied with the kit and the contents were frozen. A lyophilizer or rotary vacuum device was used to reduce the volume of the cDNA sample to 200 $\mu$l or less. Then the volume was made up to 200 $\mu$l by addition of sterile water. The cDNA was precipitated by addition of 22 $\mu$l of 2M sodium acetate and 450 $\mu$l of cold ethanol. The tube contents were frozen on dry ice, then thawed and centrifuged for 10–15 minutes. The ethanol supernatant was removed and the pellet was resuspended in 100 $\mu$l of sterile water. The cDNA was then phenol/chloroform extracted in an equal volume of phenol/chloroform. The aqueous phase was separated and 12 $\mu$l of 2M sodium acetate and 225 $\mu$l of cold ethanol were added and mixed to precipitate the cDNA. The solution was frozen, thawed, and centrifuged, as previously described, to collect the cDNA pellet. The ethanol supernatant was removed and then the pellet was washed in 80% ethanol as previously described.

Molecular Cloning in $\lambda$gt11 Cloning Vector

The double-stranded cDNA was then cloned in the phage $\lambda$gt11 cloning vector. R. Young & R. Davis, 80 Proc. Nat'l Acad. Sci USA 1194–98 (1983); T. Hyynh et al., in 1 *DNA Cloning: A Practical Approach* 49–78 (D. Glover, ed, IRL Press, Oxford, 1985). The EcoRI cloning site in this vector is located within the *E. coli* lacZ gene that was inserted into the phage $\lambda$ DNA in making the $\lambda$gt11 vector. The *lacZ* gene codes for the enzyme $\beta$-galactosidase. DNA fragments inserted into this gene by cloning at the EcoRI site result in fusion genes that make an inactive recombinant $\beta$-galactosidase enzyme under the control of the lac promoter. Recombinant phage can be recognized and selected by their inability to form blue-colored plaques on indicator plates containing the lactose analog 5-bromo-4-chloro-3-indolyl-$\beta$-D-galactoside (X-gal). Lambda gt11 phage are lac+ and thus able to cleave colorless X-gal into metabolites that self-assemble into a blue-colored indole compound. EcoRI-digested, dephosphorylated $\lambda$gt11 DNA was obtained from Invitrogen.

The cDNA was then ligated to the $\lambda$gt11 DNA. The ligation reaction contained an effective amount of $\lambda$gt11 DNA arms, cDNA, 0.1 volume of 10× ligation buffer, 0.5 $\mu$l of T4 DNA ligase, and enough water to make the final volume of 5–20 $\mu$l. The reaction was incubated at least 4 hours at 15° C. Then, the ligated DNA was concentrated by precipitation with 0.1 volume of 2M sodium acetate and 2 volumes of ethanol. The DNA was chilled, centrifuged, and the ethanol completely removed, as described above.

Ligated DNA was then packaged in the "PACKA-GENE" phage $\lambda$ packaging system obtained commercially from Promega Corp. (Madison, Wis.). This packaging procedure is described in Technical Bulletin No. 005 issued by Promega Corp. Briefly, the "PACKA-GENE" extract was permitted to thaw in an ice bath. Then, about 0.5 $\mu$l of ligated DNA was added to the extract and mixed gently. The extract and ligated DNA were incubated together at room temperature for about 2 hours. Phage buffer (20 mM Tris.HCl, pH 7.4, 100 mM NaCl, 10 mM MgSO$_4$) was added to raise the volume to 0.5 ml. Chloroform (25 $\mu$l) was added, gently mixed by inversion, and then allowed to settle to the bottom of the tube.

The titer of packaged phage was determined as described in Technical Bulletin No. 006 of Promega Corp. The recombinant phage was diluted in phage buffer. Then, 100 $\mu$l of diluted phage was mixed with 100 $\mu$l of *E. coli* Y1090 bacteria and the phage were allowed to adsorb to the bacterial cells for 30 minutes at 37° C. Three ml of molten TB top agar (45° C.) was added, mixed, and immediately poured on LB plates. (TB top agar is made by mixing 1.0 g of Bacto-Tryptone, 0.5 g of NaCl, and 0.8 g of Bacto-Agar and adding water to 100 ml, heating to melt the agar, cooling to 60° C. and adding 1 ml of 1M MgSO$_4$. LB agar is made by mixing 10 g of Bacto-Tryptone, 5 g of Bacto-yeast extract, 5 g of NaCl, 15 g of Bacto-agar, water to raise the volume to 1 liter, and NaOH to adjust the pH to 7.5.) The top agar was permitted to harden before inverting the plates and incubating at 37° C. overnight. Then the number of plaques was counted and the titer of phage calculated.

Isolation of Recombinant Antigen

Recombinant antigen was isolated using a nonradioactive immunoblotting technique described in the technical manual for the "PROTOBLOT" Immunoscreening System from Promega Corp. In this technique, Y1090 host cells were infected with $3 \times 10^4$ plaque forming units of recombinant phage from the $\lambda$gt11 library and then plated on agar plates. The plates were incubated for 3.5 hours at 42° C. and then overlaid with dry nitrocellulose filters previously saturated with 10 mM IPTG and incubated for another 3.5 hours at 37° C. During the incubation of the nitrocellulose filters with the agar plates, phage and proteins released from lytically-infected cells adhered to the filters. The filters were removed from the plates and then blocked to prevent other proteins from adhering to the plates. Blocking was achieved by incubating the filters for 15–30 minutes in TBST buffer (10 mM Tris.HCl, pH 8.0, 1 mM EDTA, 0.05% Tween-20) containing 5% nonfat dry milk to saturate nonspecific binding sites on the nitrocellulose filters. Serum (diluted 1:20 with TBST buffer) from a patient clinically determined to have rheumatoid arthritis was then incubated with the filter for 30 minutes. Then, the filter was thrice washed in 15–20 ml of TBST for 5–10 minutes each to remove antibodies that were bound nonspecifically. Then the filter was incubated with an anti-IgM antibody-alkaline phosphatase conjugate (Kirkegaard & Perry Laboratories, Inc., Gaithersburg, Md.; diluted 1:100 with TBST) for 30 minutes at room temperature. The filter was then washed again by the same method described above. Then 5 ml of the color development substrate solution, containing 33 $\mu$l of nitro blue tetrazolium (NBT, 50 mg/ml in 70% dimethylformamide) and 16.5 $\mu$l of 5-bromo-4-chloro-3-indolyl phosphate (BCIP, 50 mg/ml in dimethylformamide), was added. Positive plaques produced a dark purple color within a few minutes as a result of alkaline phosphatase activity. Color development was stopped by placing the filter in 20 mM Tris.HCl, pH 8.0, 5 mM EDTA. Positive plaques were retested and purified by taking a small agar plug from the region of the plate corresponding to the positive signal on the filter. Phage particles were eluted from the agar plug by incubating in 1 ml of phage diluent (10 mM Tris.HCl, pH 7.5, 10 mM MgCl$_2$) for at least 60 minutes with occasional mixing by vortexing. An aliquot of the phage diluent containing eluted phage particles was plated and screened by the same procedure described above. This process of taking an agar plug and replating was repeated until all of the plaques on a test plate yielded a positive signal.

Recloning and Expression in a Bacterial Plasmid Vector

A lysogen of a purified positive recombinant λgt11 phage was generated according to Technical Bulletin No. 006 of Promega Corp. Briefly, late log phase *E. coli* T1089 cells were infected with recombinant λgt11 phage at a multiplicity of infection of about 5 for 20 minutes at 32° C. Then cells were plated on LB plates at a density of about 200 colonies per plate and incubated at 32° C. Single colonies were tested by streaking onto 2 LB plates. One plate was incubated at 42° C. and the other at 32° C. Clones which grew at 32° C. but not at 42° C. were assumed to be lysogens.

Recombinant phage DNA was isolated from the λgt11 lysogen, using an alkaline lysis miniprep protocol described in T. Maniatis et al., *Molecular Cloning: A Laboratory Manual* (Cold Spring Harbor Laboratories, Cold Spring Harbor, N.Y., 1982). Briefly, 100 ml of lysogen culture was centrifuged for 10 minutes at 5000 rpm to pellet the cells. The cell pellet was resuspended in 3 ml of buffer containing 50 mM glucose, 10 mM EDTA, 25 mM Tris.HCl (pH 8.0) and 5 mg/ml lysozyme. The suspension was stored at room temperature for 5 minutes. Then, 4 ml of freshly prepared, ice-cold solution of 0.2N NaOH and 1% SDS was added and incubated in ice for 10 minutes. After adding 3 ml of icecold solution of 3M potassium acetate (pH 4.8), the suspension was incubated in ice for another 15 minutes. A precipitate was centrifuged down at 10,000 rpm and 1 volume of isopropanol was added to the supernatant. After 10 minutes at room temperature, the DNA was pelleted by centrifugation at 5000 rpm. The pellet was dissolved in 500 μl of sterile distilled water. The DNA was purified further by adding 7.5 m ammonium acetate and incubating in ice for 30 minutes. The precipitate was removed by centrifugation at 10,000 rpm and the DNA was reprecipitated with 1 volume of isopropanol. After washing with 70% ethanol, the DNA was dissolved in sterile distilled water and digested with EcoRI. The DNA fragments were electrophoretically fractionated in a 0.7% low melting agarose gel. Upon ethidium bromide staining and ultraviolet illumination, a unique 2600 bp band was revealed. This band was sliced from the gel and the agarose was melted at 70° C. The DNA was then phenol extracted and precipitated with alcohol.

The 2600 bp EcoRI fragment was then recloned, using standard procedures, at the EcoRI site of the plasmid expression vector pTrcHis C, obtained from Invitrogen. This vector has the same reading frame as λgt11, contains all the DNA sequences to obtain high level protein expression in *E. coli*, and also contains a sequence encoding 6 consecutive histidine residues, which allow the expressed protein to bind Ni-charged "PROBOND" resin (Invitrogen) so that the recombinant protein can be easily purified in a one-step procedure. The pTrcHis C plasmid containing the 2600 bp fragment was transformed into *E. coli* strain Top10 (obtained from Invitrogen).

Expression of the recombinant protein was demonstrated by Western blot analysis. Transformants were grown in Luria Broth (LB) at 37° C. to an OD$_{600}$ of 0.5. Then isopropylthio-β-D-galactoside (IPTG), a gratuitous inducer of the lac operon, was added to a final concentration of 1 mM to induce expression of the recombinant protein. The transformants were grown an additional 3 hours at 30° C. after induction. Then about 200 μl of culture was placed in a microfuge tube and centrifuged briefly to pellet the cells. The broth was removed and discarded and the pellet was resuspended in SDS-containing buffer. T. Maniatis et al., supra. The samples were heated for 2 minutes in a boiling water bath and loaded on a 10% SDS-polyacrylamide gel and electrophoresed overnight at 70 volts. T. Maniatis et al., supra. The proteins were transferred electrophoretically to a nitrocellulose membrane using the "POLYBLOT" Electrotransfer System according to the instruction manual (American Bionetics, Inc., Hayward, Calif.). Briefly, a filter paper was soaked in anode buffer no. 1 (0.3M Tris, pH 10.4, 20% methanol). Then, a filter paper soaked in anode buffer no. 2 (25 mM Tris, pH 10.4, 20% methanol) was placed on the first filter paper. A nitrocellulose membrane was wetted with distilled water and placed on the second filter paper. The gel was placed on the nitrocellulose membrane. Then, a filter paper soaked in cathode buffer 25 mM Tris, 40 mM 6-aminohexanoic acid, 20% methanol, pH 9.4) was placed on the gel. This sandwich of filter papers, gel and nitrocellulose membrane was then placed in the "POLYBLOT" apparatus and electric current was applied according to the guidelines in the instruction manual. After transfer was complete, the membrane was removed and then blocked to prevent nonspecific binding of proteins, as described above. Serum (diluted 1:21) from a patient with rheumatoid arthritis was added to the membrane and incubated for 1 hour. The membrane was then washed 3 times for 5 minutes each in TBST. Then the membrane was incubated with anti-IgM antibody-alkaline phosphatase conjugate (Kirkegaard & Perry) for 30 minutes, as described before in the plaque screening procedure. The membrane was then washed 3 times in TBST to remove nonspecifically bound antibody. Then the color was developed by addition of NBT and BCIP, as described above.

These tests revealed a single band corresponding to a protein of about 48 kD that reacted with the reference serum. About 4 kD of the protein sequence is derived from the plasmid vector, suggesting that the remaining 44 kD of protein produced by the expression vector is from the antigen that reacts with serum from a rheumatoid arthritis patient.

Purification of Recombinant Antigen from Bacteria

The recombinant protein expressed by the bacterial plasmid expression vector was purified using an Invitrogen "PROBOND" column according to the instructions supplied with the column. About 1 liter of LB also containing glucose and 50 μg/ml ampicillin was inoculated with 10 ml of an overnight culture of Top10 cells containing the expression plasmid. The cells were grown for 2.5 hours, at which time IPTG was added to a final concentration of 1 mM to induce expression of the recombinant protein. The cells were incubated an additional 3 hours at 37° C. after induction. Then the cells were harvested by centrifugation and the pellet was suspended in 20 ml of a buffer containing 20 mM sodium phosphate and 500 mM NaCl, pH 7.8. Lysozyme was added to a concentration of 1 mg/ml, the cells were incubated for 30 minutes, then the cells were lysed by sonication. The cells were then centrifuged at 10,000 rpm; the recombinant protein was insoluble and remained in the pellet. The recombinant protein was only partially soluble in either 6M guanidinium or 8M urea, therefore expression in insect cells was used to solve the solubility problem.

Recloning and Expression in a Baculovirus Vector

The pBlueBacHis C vector (Invitrogen) is designed for efficient protein expression and purification from recombinant baculovirus clones in insect cells. High levels of expression of DNA sequences cloned into the pBlueBacHis C vector is made possible by the presence of the polyhedrin promoter. Polyhedrin protein is the major structural component of baculovirus occlusion bodies and accounts for more than 50% of the total "stainable" protein on infected *Spodoptera frugiperda* cells on SDS-polyacrylamide gels. The vector contains the natural polyhedrin leader sequence followed by a sequence which codes for an ATG translation initiation codon, a tract of 6 histidine residues that function as a metal binding domain in the translated protein, a transcript stabilizing sequence from gene 10 of phage T7, and an enterokinase cleavage recognition sequence. A multiple cloning region positioned downstream of this sequence allows insertion of the foreign gene in the correct reading frame relative to the initiation codon. This vector also allows co-expression of β-galactosidase upon transfection, enabling rapid identification of recombinant plaques in the presence of substrates such as X-gal or Bluo-gal.

For expression of the recombinant antigen in the baculovirus system, the plasmid pTrcHis C containing the 2600 bp insert was digested with both BamHI and EcoRI restriction endonucleases. The 2600 bp fragment that was released was separated on low melting 0.7% agarose gel as described above. The DNA was then isolated from the agarose using the "SPELLBIND" DNA extraction unit according to the instructions provided with the unit (FMC, Rockland, Me.). To obtain the correct reading frame as in the λgt11 and pTrcHis C clones, the fragment was subcloned at the corresponding site of baculovirus transfer vector pBlueBacHis C (Invitrogen). Since this vector was derived from an *E. coli* pUC plasmid vector, all manipulations were done in *E. coli* Top10 (Invitrogen). All recloning steps were done according as described above or in T. Maniatis et al., supra.

Sequences which flank the polyhedrin gene in the wild-type baculovirus genome are positioned to flank the expression cassette on the pBlueBacHis C transfer vector. Following co-transfection of pBlueBacHis C and wild-type viral DNA, homologous recombination between these sequences results in a recombinant virus with the gene of interest expressed under the control of the viral polyhedrin enhancer/promoter elements. "BACULOGOLD" linearized baculovirus DNA (Pharmingen, San Diego, Calif.) was used as the "wild-type" DNA for cotransfection with pBlueBacHis C. "BACULOGOLD" DNA contains a lethal deletion, thus the transfected virus DNA cannot make infectious virus particles in insect cells unless the deletion is complemented by co-transfected polyhedrin-based pBlueBacHis C. The recombinant virus was produced in Sf9 insect cells and purified as described in the Invitrogen manual. Briefly, $2 \times 10^6$ Sf9 cells were seeded onto a 60 mm plate and allowed to attach for at least 30 minutes. Then, "BACULOGOLD" and pBlueBacHis C DNA containing the 2600 bp insert were mixed with cationic liposome solution to produce a transfection mix. Then, the transfection mix was used to replace the medium of the insect cells. The cells were then incubated at 27° C. in a humidified environment for 48 hours. Then the medium was removed from the insect cells and stored as the virus stock to be used for identification of recombinant virus by plaque assay. The virus stock was then used to prepare 10-fold dilutions for plaque purification of recombinant virus according to the Invitrogen manual. Blue plaques that failed to produce occlusion bodies were selected for purification and propagation.

Expression of the 2600 bp DNA fragment in pBlueBacHis C was confirmed by Western Blot analysis. About 1 ml of Sf9 insect cells infected 3 days earlier with virus containing the recombinant plasmid were pelleted and dissolved in 100 μl of Laemmli buffer. U. Laemmli, 227Nature 680–85 (1970). The sample was boiled for 2 minutes and then loaded on a 7.5% SDS-polyacrylamide gel and electrophoresed overnight at 70 volts, as described above. The protein was transferred electrophoretically to a nitrocellulose membrane, as described above. Nonspecific binding of protein was blocked by treating the membrane with 5% nonfat dry milk in TBST, as described above. Serum from a rheumatoid arthritis patient was added to the membrane-bound protein at a dilution of 1:21 and incubated for 1 hour. The membrane was then washed 3 times with TBST and incubated with anti-human IgM-alkaline phosphatase conjugate for 30 minutes. The membrane was again washed 3 times with TBST before color development substrate solution was added. A single protein band of about 100 kd reacted with the serum from the rheumatoid arthritis patient. About 6 kd represents the vector-derived protein sequences. Therefore, the size of the protein expressed in baculovirus-infected insect cells is 94 kd. The predicted size of the protein, based on the size of the DNA insert is about 94 kd. This suggests that the full-length DNA sequence is expressed in the baculovirus expression system but was not in *E. coli*.

Purification of Recombinant Protein from Insect Cells

Recombinant antigen, such as that expressed in the recombinant baculovirus expression system described above, was purified from the insect cell culture by affinity chromatography.

As mentioned above, pBlueBacHis C contains a nucleotide sequence downstream from the translation start codon which produces 6 consecutive histidine residues in the N-terminal region of the expressed protein. This region has affinity to bind Ni-charged "PROBOND" resin and, thus, permit one-step purification. The recombinant protein was produced and purified according to the Invitrogen manual. A 50 ml culture of Sf9 insect cells was grown to a density of $2 \times 10^6$ cells/ml in a 100 ml spinner flask. Cells were infected with high-titer viral stock and then incubated for 3 days. The cells were harvested by centrifugation and resuspended in a buffer containing 20 mM sodium phosphate, pH 7.8, and 500 mM NaCl. Then the cells were lysed by sonication and cell debris was removed by centrifugation. The clarified supernatant was then passed over a "PROBOND" column. The polyhistidine-containing fusion proteins bound to the Ni-containing ligands of the "PROBOND" column whereas the majority of host cell proteins did not bind. The column was washed with native wash buffer (20 mM sodium phosphate, pH 6.3, 500 mM NaCl) to remove host cell proteins which did happen to bind to the resin. Then, the recombinant protein was eluted with either denaturing elution buffer (8M urea, 20 mM sodium phosphate, pH 4.0, 500 mM NaCl) or a 20-200 mM imidizole gradient in native wash buffer. Affinity chromatography purification on "PROBOND" columns was done according to the Invitrogen manual.

Unlike the recombinant protein expressed in *E. coli*, the protein expressed in insect cells and purified on the "PROBOND" column was highly soluble. A single protein band of about 100 kd was visible in stained SDS-polyacrylamide gels. About 1.5 mg of protein was obtained from 50 ml of culture.

ELISA Test of the Recombinant Protein

About 100 µl of protein solution (1 µg/ml of purified recombinant protein in PBS buffer, pH 7.4) was placed in a well of a polystyrene microtiter plate (High binding 96 well Corning plate) and incubated overnight at 4° C. The plate was washed 2 times with 200 µl of a wash buffer containing 10 mM Tris.HCl, pH 8.0, 1 mM EDTA, 150 mM NaCl, and 0.05% Tween-20 at room temperature for 5 minutes. The plate was blocked overnight at 4° C. with 300 µl of 0.1% nonfat dry milk in the wash buffer to prevent nonspecific binding to the plate. A 100 µl aliquot of serum diluted 1:21 with wash buffer was added to the well and incubated for 1 hour at 37° C. Then the well was washed 3 times for 5 minutes at 37° C. with wash buffer. A 100 µl aliquot of alkaline phosphatase-conjugated anti-human IgM (Kirkegaard & Perry) was added to the well and incubated for 1 hour at 37° C. The well was then washed 3 times with wash buffer for 5 minutes at 37° C. Then 100 µl of alkaline phosphatase substrate, prepared by adding 5 mg of p-nitrophenolphosphate and 1 ml of 5× diethanolamine buffer (supplied by Kirkegaard and Perry) to 4 ml of distilled water, was added to the well and incubated at 37° C. for 15 minutes. Then, the optical density was measured at 405 nm.

Sera from 60 patients with clinical symptoms of rheumatoid arthritis (35 were seropositive and 25 were seronegative for Rf), 20 individuals seropositive for an anti-DNA disease marker for SLE, and 20 healthy individuals were tested by the method outlined above. The results of these tests are summarized in the following table wherein RAMA represents the Rheumatoid Arthritis IgM-associated Antigen of the instant invention, encoded by the plasmid deposited as ATCC 69605.

| Serum | Total | RAMA+ | RAMA− | Percent |
|---|---|---|---|---|
| Rf+ | 35 | 34 | 1 | 97 |
| Rf− | 25 | 11 | 14 | 44 |
| Anti-DNA+ | 20 | 3 | 17 | 15 |
| Healthy | 20 | 0 | 20 | 0 |

Serum from all of the healthy subjects showed ELISA values below 0.250. Thus, a reading of 0.250 was taken as the cut-off value to determine a positive reaction. Of the 35 sera from seropositive rheumatoid arthritis patients, 34 or 97% showed ELISA values above 0.250 and, thus, were deemed to give a positive reaction. Of the 25 sera from seronegative rheumatoid arthritis patients, 11, or 44%, showed ELISA values above 0.250 and, thus, were deemed to give a positive reaction. Three of the 20 Anti-DNA+ control sera also gave positive reactions. Therefore, these results show that almost all of seropositive rheumatoid arthritis patients could be diagnosed with the aid of this ELISA test to detect the presence of antibodies in the serum against the recombinant RAMA antigen. Further, almost half of seronegative rheumatoid arthritis patients could be diagnosed as well. These results suggest that about 85% of rheumatoid arthritis cases could be diagnosed using this invention as compared to only about 70% using the standard Rf test.

A deposit of an *E. coli* strain containing a plasmid bearing a gene encoding the recombinant RAMA antigen described herein and used for diagnosing rheumatoid arthritis was deposited on Apr. 13, 1994, with the following International Depository Authority: American Type Culture Collection, 12301 Parklawn Drive, Rockville, Md. 20852 USA. The accession number of the deposited strain is ATCC 69605.

I claim:

1. A method for diagnosing rheumatoid arthritis comprising the steps of:
(a) providing a recombinant RAMA antigen that is specifically detectable by rheumatoid arthritis-associated IgM antibodies;

(b) incubating said RAMA antigen with patient serum to form a complex of said RAMA antigen and said IgM antibodies; and (c) detecting said complex as a measure of said IgM antibodies against said RAMA antigen in patient sera.

2. The method as in claim 1 wherein providing said recombinant RAMA antigen comprises the preliminary steps of:

(a) making a cDNA library from polyadenylated RNA purified from human cells, wherein said library is prepared by randomly cloning cDNA derived from said polyadenylated RNA in a cloning vector such that recombinant vectors are produced;

(b) selecting recombinant vectors that express said recombinant RAMA antigen;

(c) expressing said recombinant RAMA antigen in a host containing the recombinant vector; and (d) purifying the recombinant RAMA antigen.

3. The method as in claim 2 wherein step (a) further comprises making a cDNA library from polyadenylated RNA purified from an Epstein-Barr virus-transformed human B lymphocyte cell line.

4. The method as in claim 3 wherein the Epstein-Bar virus-transformed cell line is the Raji cell line.

5. The method as in claim 2 wherein step (a) further comprises purifying the polyadenylated RNA by oligo(dT) cellulose chromatography.

6. The method as in claim 2 wherein step (a) further comprises cloning the cDNA library using phage λgt11 as the cloning vector.

7. The method as in claim 2 wherein step (b) further comprises selecting said recombinant vectors that express said recombinant RAMA antigen by permitting antibodies in sera from clinically-confirmed rheumatoid arthritis patients to bind to said RAMA antigen and then detecting said bound antibodies.

8. The method as in claim 7 wherein said bound antibodies are detected colorimetrically by binding an IgM anti-human antibody-alkaline phosphatase conjugate and providing one or more alkaline phosphatase color development substrates.

9. The method as in claim 8 wherein the color development substrates are nitro blue tetrazolium and 5-bromo-4-chloro-3-indolyl phosphate.

10. The method as in claim 2 wherein step (c) further comprises growing host cells containing the recombinant vector to an optimum cell density and then inducing expression of the recombinant RAMA antigen.

11. The method as in claim 10 wherein induction of expression is by addition of IPTG to the nutrient medium.

12. The method as in claim 2 wherein step (c) further comprises expressing said recombinant RAMA antigen in *E. coli* cells.

13. The method as in claim 2 wherein step (c) further comprises expressing said recombinant RAMA antigen in insect cells.

14. The method as in claim 2 further comprising a step intermediate between steps (b) and (c) wherein cloned cDNA from a selected recombinant vector is recloned in a plasmid expression vector.

15. The method as in claim 14 wherein the plasmid expression vector contains nucleotides encoding a metal binding domain having high affinity for an affinity chromatography matrix containing a metal moiety.

16. The method as in claim 15 wherein the plasmid expression vector is a baculovirus vector capable of protein expression in insect cells.

17. The method as in claim 2 wherein step (d) further comprises purifying said recombinant RAMA antigen by affinity chromatography.

18. The method as in claim 17 wherein said recombinant RAMA antigen contains residues comprising a metal binding domain that has high affinity for an affinity chromatography matrix containing a metal moiety.

19. The method as in claim 18 wherein the affinity chromatography matrix contains a metal moiety and is capable of reversibly binding said metal binding domain.

20. The method as in claim 1 wherein step (b) further comprises detecting by reacting said complex with an enzyme-labeled anti-IgM antibody.

21. The method as in claim 20 wherein said RAMA antigen is attached to a solid surface and then patient sera are tested for the presence of antibodies that bind said antigen.

22. The method as in claim 21 wherein the enzyme is alkaline phosphatase.

23. The method as in claim 22 wherein anti-IgM antibody bound to said complex is detected by reacting said alkaline phosphatase with p-nitrophenylphosphate.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 13 nucleotides
( B ) TYPE: nucleic acid
( C ) STRANDEDNESS: single
( D ) TOPOLOGY: linear ( i i ) MOLECULE TYPE: synthetic linker ( x i ) SEQUENCE DESCRIPTION: SEQ ID NO:1:

AATTCGCGGC CGC    13